(12) United States Patent
Woelfel et al.

(10) Patent No.: US 10,371,833 B2
(45) Date of Patent: Aug. 6, 2019

(54) X-RAY DETECTOR HAVING A LIGHT SOURCE ON THE CARRIER ELEMENT

(71) Applicant: Siemens Healthcare GmbH, Erlangen (DE)

(72) Inventors: Stefan Woelfel, Dormitz (DE); Alfons Eismann, Pinzberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/978,371

(22) Filed: May 14, 2018

(65) Prior Publication Data

US 2018/0335529 A1 Nov. 22, 2018

(30) Foreign Application Priority Data

May 17, 2017 (EP) ..................................... 17171522

(51) Int. Cl.
*G01T 1/24* (2006.01)
*A61B 6/03* (2006.01)
*A61B 6/00* (2006.01)
*G01T 1/20* (2006.01)

(52) U.S. Cl.
CPC ............. *G01T 1/244* (2013.01); *A61B 6/032* (2013.01); *A61B 6/4233* (2013.01); *A61B 6/4291* (2013.01); *A61B 6/4488* (2013.01); *G01T 1/2018* (2013.01); *G01T 1/24* (2013.01); *G01T 1/247* (2013.01)

(58) Field of Classification Search
CPC ....... A61B 6/4258; A61B 6/037; G01T 7/005; G01T 1/247; G01T 1/24; G01T 1/249; G01T 1/005
See application file for complete search history.

(56) References Cited

U.S. PATENT DOCUMENTS

| | | | | |
|---|---|---|---|---|
| 5,025,462 A | * | 6/1991 | Saito | ..................... G01T 1/2018 250/361 R |
| 7,723,693 B2 | * | 5/2010 | Okada | ................... G01T 1/2018 250/370.01 |
| 2002/0024016 A1 | * | 2/2002 | Endo | ..................... G01T 1/2928 250/370.11 |
| 2007/0131867 A1 | | 6/2007 | Okada et al. | |

(Continued)

FOREIGN PATENT DOCUMENTS

| | | |
|---|---|---|
| DE | 102010015422 A1 | 10/2011 |
| DE | 102011080892 B3 | 2/2013 |
| DE | 102013214684 A1 | 1/2015 |

OTHER PUBLICATIONS

European Search Report for European Application No. EP17171522 dated Oct. 26, 2017.

*Primary Examiner* — Yara B Green
(74) *Attorney, Agent, or Firm* — Harness, Dickey & Pierce, P.L.C.

(57) ABSTRACT

An X-ray detector includes a converter element and a carrier element in a stack arrangement. In an embodiment, the X-ray detector further includes a light source arranged on the carrier element, a light-directing unit formed outside a projection of a planar extension of the converter element in the stacking direction, and a light-directing unit arranged such that a quantity of light emitted from the light source is incident on a surface of the converter element, facing away from the carrier element via a light path.

22 Claims, 3 Drawing Sheets

(56) References Cited

U.S. PATENT DOCUMENTS

2011/0253886 A1  10/2011  Hackenschmied et al.
2014/0284456 A1   9/2014  Okada et al.
2015/0030120 A1   1/2015  Ergler et al.

* cited by examiner

X-RAY DETECTOR HAVING A LIGHT SOURCE ON THE CARRIER ELEMENT

PRIORITY STATEMENT

The present application hereby claims priority under 35 U.S.C. § 119 to European patent application number EP17171522.0 filed May 17, 2017, the entire contents of which are hereby incorporated herein by reference.

FIELD

At least one embodiment of the invention generally relates to an X-ray detector and/or a medical device for this purpose, wherein the X-ray detector in at least one embodiment has a light source arranged on the carrier element which illuminates a converter element of the X-ray detector via a light path.

BACKGROUND

In X-ray imaging, for example, in computed tomography, angiography or radiography, counting directly-converting X-ray detectors or integrating indirectly-converting X-ray detectors can be used.

In indirectly-converting X-ray detectors, X-ray radiation or photons can be converted into light by a suitable converter material and into electric pulses via photodiodes. Scintillators, for example, GOS ($Gd_2O_2S$), CsJ, YGO or LuTAG, are frequently used as converter material. Scintillators are particularly used in the energy range up to 1 MeV in medical X-ray imaging. Usually, so-called indirectly-converting X-ray detectors, so-called scintillator detectors, are used, in which the conversion of the X-rays or gamma rays into electrical signals takes place in two stages. In a first stage, the X-ray or gamma quanta are absorbed in a scintillator element and converted into optically visible light; this effect is called luminescence. In a second stage, the light induced by luminescence is then converted into an electrical signal by a first photodiode optically coupled to the scintillator element, read out by way of evaluation or readout electronics and then forwarded to an arithmetic unit.

In directly-converting X-ray detectors, the X-ray radiation or the photons can be converted into electric pulses by a suitable converter material. A converter element comprises the converter material. CdTe, CZT, CdZnTeSe, CdTeSe, CdMnTe, InP, $TlBr_2$, $HgI_2$, GaAs or others can be used as converter material, for example. A voltage is applied to the converter element such that the electron-hole pairs triggered by the X-ray radiation and/or photons can be separated. The electrical charge of the electrons or holes is forwarded to the evaluation electronics as an electric pulse. The electric pulses are assessed by the evaluation electronics, for example an integrated circuit (Application Specific Integrated Circuit, ASIC). In counting X-ray detectors, incident X-ray radiation is measured by counting the electric pulses which are triggered by the absorption of X-ray photons in the converter material. As a rule, the level of the electric pulse is proportional to the energy of the absorbed X-ray photon. As a result, spectral information can be extracted by comparing the level of the electric pulse with a threshold value.

The converter material can have drift characteristics which have an impact as a drift effect and/or change in the count values of the evaluation electronics and can thus produce unwanted image artifacts. These drift characteristics can be improved by way of additional illumination. The converter material can be, for example, conditioned, i.e. a predetermined condition produced, by way of the additional illumination. As a result of this conditioning, imperfections in the converter material can be reduced accordingly.

An X-ray detector is known from the publication DE 10 2010 015 422 A1 comprising a directly-converting semiconductor layer for the conversion of incoming radiation into electrical signals with a band gap energy characteristic of the semiconductor layer and at least one light source for coupling of light into the semiconductor layer, wherein the generated light has an energy above the band gap energy of the semiconductor layer for the simulation of incoming X-ray quanta. Furthermore, it comprises at least one evaluation unit for calculating an evaluation signal from the electrical signals generated when coupling the light into the semiconductor layer and at least one calibration unit for calibrating at least one pulse discriminator based on the evaluation signal. This will create the preconditions for a rapidly repeatable calibration of the X-ray detector, taking into consideration the current polarization state without the use of X-ray radiation.

A directly-converting X-ray radiation detector, particularly for use in CT systems, is known from the publication DE 10 2011 080 892 B, having at least one semiconductor material used for the detection of X-ray radiation. A scintillation layer is applied to at least one of the sides of the semiconductor material facing the X-ray radiation, wherein the X-ray radiation generates optical radiation in the scintillation layer.

A directly-converting X-ray detector for the detection of X-ray radiation is known from the publication DE 10 2013 214 684 A1, having a direct converter used for the detection of X-ray radiation, at least one collimator arranged at least partially in the direction of radiation of the X-ray radiation before the direct converter and at least one radiation source which is arranged laterally of the direct converter and indirectly irradiates the direct converter with additional radiation, wherein the at least one collimator has at least one reflexive coating on a side facing the direct converter, on which the additional radiation is reflected onto the direct converter, and having a cooling device by which the at least one radiation source can be cooled.

The radiation source and/or light source was hitherto soldered onto for example printed circuit board material, which was mounted on the collimator and/or anti-scatter grid via clamping or bonding laterally between the side of the anti-scatter grid facing the converter element and the plane of the surface of the converter element facing the anti-scatter grid.

SUMMARY

The inventors have realized that the dissipation of the heat arising in the light source cannot be sufficient as a result of this design and/or arrangement. The size and/or the volume of the printed circuit board can only be very limited as the beam path of the X-ray radiation between anti-scatter grid and converter element should not be affected by the printed circuit board in order to avoid a non-image-effective dose deposition in the patient.

In addition, the inventors have realized that the thermal conductivity of printed circuit boards is too low as a rule, so that the dissipation of the heat via the anti-scatter grid is insufficient. In addition, the thermal connection of the anti-scatter grid to a large heat accumulator and/or heat sink or to an area remote from the anti-scatter grid in which effective cooling, for example via (cooling) air, can be achieved, may be insufficient.

The inventors have recognized that, as a result of insufficient heat dissipation and/or insufficient cooling, the quantity of light is limited as the light source can become too hot when larger quantities of light are radiated and the so-called SOA (Safe Operation Area) can be exceeded, whereby the service life of the light source, for example LEDs, and consequently the service life of the X-ray detector, is restricted.

As a result of this limitation of the quantity of light, insufficient light output may be supplied to the converter material in order to condition it even better. The negative drift characteristics can only be reduced insufficiently and it is hardly possible to guarantee a permanently good image quality during operation, so that the counting rate drift of the evaluation unit can lead to correspondingly negative image artifacts.

At least one embodiment of the invention provides an X-ray detector and a medical device which enable improved cooling of the light source in order to improve the signal stability of the X-ray detector.

At least one embodiment of the invention is directed to an X-ray detector and/or a medical device.

At least one embodiment of the invention relates to an X-ray detector having a converter element and a carrier element in a stack arrangement, wherein a light source is arranged on the carrier element, and a light-directing unit is formed outside a projection of the planar extension of the converter element in the stacking direction. The light-directing unit is arranged such that a quantity of light emitted by the light source is incident on a surface of the converter element facing away from the carrier element by way of a light path.

At least one embodiment of the invention further relates to a medical device having an X-ray detector according to the invention. The advantages of the X-ray detector according to at least one embodiment of the invention can be transferred to the medical device. Advantageously, image artifacts can be reduced.

According to at least one embodiment of the invention, the medical device is a computed tomography system.

BRIEF DESCRIPTION OF THE DRAWINGS

Example embodiments of the invention are explained in more detail hereinafter with reference to drawings. The drawings show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor;

however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an X-ray detector having a converter element and a carrier element in a stack arrangement, wherein a light source is arranged on the carrier element, and a light-directing unit is formed outside a projection of the planar extension of the converter element in the stacking direction. The light-directing unit is arranged such that a quantity of light emitted by the light source is incident on a surface of the converter element facing away from the carrier element by way of a light path.

The X-ray detector can in particular be a directly-converting or counting X-ray detector. The converter element can in particular comprise CdTe or CZT. The X-ray detector can have a plurality of pixel elements. The converter element can be electrically conductively connected to an evaluation unit via solder joints. The evaluation unit can comprise the evaluation electronics. The evaluation unit can be connected, in particular electrically conductively, to the carrier element.

The carrier element can have evaluation elements, for example for merging or separating data streams. The carrier element can in particular be assigned to a plurality of converter elements or a plurality of evaluation units. The carrier element can be a carrier ceramic. The evaluation unit can be directly connected, particularly electrically conductively, to the carrier element and/or the carrier ceramic. The carrier element can be a so-called module backplane. The evaluation unit can be indirectly connected, particularly electrically conductively, to the carrier element and/or the module backplane by way of a further carrier element.

The stack arrangement can have the following elements in the following sequence: any anti-scatter grid, any light diffuser, converter element, any evaluation unit, any further carrier element and carrier element.

In particular, the converter element has a planar extension perpendicular to the direction of radiation incidence of the X-ray radiation. The planar extension is essentially formed in the stack plane. The surface formed by the planar extension can be referred to as the radiation incidence surface. The converter element has a surface normal which is aligned perpendicular to the planar extension. The stacking direction essentially runs parallel to the surface normal. The projection of the planar extension of the converter element runs in the stacking direction such that the planar extension of the converter element is projected in a viewing direction along the stacking direction into another plane.

The light source emits a quantity of light which is in particular, predetermined or/and adjustable. The light source is connected to a light-directing unit such that the quantity of light can essentially be completely coupled into the light-directing unit and/or the quantity of light can essentially be completely incident on the converter element. The quantity of light is guided along a light path to the converter element via a light-directing unit. The light path can be curved or kinked or non-linear. The quantity of light is incident on a surface of the converter element facing away from the carrier element. The surface facing away from the carrier element can in particular face away from the light source. The quantity of light cannot and/or in particular cannot be completely incident on the converter element without the light-directing unit.

The quantity of light can essentially be coupled completely into the possible light diffuser by the light-directing unit. The light-directing unit can have a smaller cross-section than the possible light diffuser perpendicular to the light path. The light-directing unit cannot be designed as the possible light diffuser. The possible light diffuser can bring about an essentially homogenous illumination of the converter element. The light-directing unit cannot bring about an essentially homogenous illumination of the converter element, particularly in the case of a light guide. The light-directing unit can only be designed to deflect the quantity of light from a course which is essentially parallel to the stacking direction along the light path to a course which is essentially parallel to the planar extension of the converter element along the light path, for example in the direction of the possible light diffuser. Advantageously, the distance between the light source and the converter element can be advantageously increased via the arrangement of the light source on the carrier element. Advantageously, heating of the converter element by the light source can be substantially reduced.

In order to enable homogenous conditioning of the planar converter element, a homogenous illumination of the surface of the converter element is necessary. An illumination of the lateral surfaces parallel to the stacking direction is not sufficient. The inventors therefore propose a light path from the light source to the surface of the converter element facing away from the carrier element.

The carrier element can have HTCC and/or LTCC ceramics. The light source is arranged on the carrier element, for example via a solder joint. Advantageously, more space for the light source and/or its arrangement and connection to the carrier element can be provided on the carrier element. Advantageously, the solder joints can be larger than is known from the publication DE 10 2013 214 684 A1, such that improved heat dissipation is made possible. The light source can be an LED.

Advantageously, as a result of the better heat dissipation of the light source, an increased quantity of light can be used, for example by increasing the flow in the LED, whereby an increased light output can be incident on the converter element. Advantageously, the conditioning of the converter element can be improved.

According to one embodiment of the invention, a planar extension of the carrier element is greater than a planar extension of the converter element. The planar converter element can be arranged opposite the carrier element such that the light source is arranged outside the projection of the planar extension of the converter element in the stacking direction and on the carrier element. Advantageously, the light source can be arranged laterally next to the evaluation unit on the carrier element.

According to one embodiment of the invention, the light source is arranged outside the projection of the converter element in the stacking direction. Advantageously, the heat of the light source can be removed in a simplified manner. Particularly advantageously, the converter element cannot be affected by the heat of the light source. Advantageously, the direction angle of the light-directing unit can be limited to, for example, 180 degrees maximum, preferably approximately 90 degrees. In particular, the light path, for example the entire path from the light source to the surface of the converter element, can have a direction angle of essentially 180 degrees maximum. Advantageously, the light-directing unit can require little space.

According to one embodiment of the invention, the light path partially runs essentially parallel to the stacking direction. The quantity of light can be guided along the light path from the plane of the carrier element at least to the plane of the converter element essentially along the stacking direction. Advantageously, the light path can be designed in a space-saving manner. The light path can partially run essentially perpendicular to the stacking direction, for example as far as the lateral edge of the converter element, or inside a light diffuser essentially parallel to the planar extension of the converter element. The light diffuser can be designed such that the quantity of light can be uniformly decoupled from the light diffuser along the planar extension of the converter element, such that a homogenous illumination of the converter element can be achieved. The light diffuser can partially comprise the light path.

According to one embodiment of the invention, the light-directing unit comprises a reflection unit. The reflection unit can be designed as a mirror. The reflection unit has at least one reflective surface. The reflection unit is designed such that the light path runs from the light source to the surface of the converter element facing away from the carrier element. The reflection unit can be arranged on the anti-scatter grid. The reflection unit can be arranged on the anti-scatter grid such that the light path runs from the light source to the reflection unit parallel to the stacking direction. The reflection unit is designed such that the light path is deflected to the surface of the converter element facing away from the carrier element or towards a course which is essentially parallel to the planar extension of the converter element. The reflection unit can be arranged between the fastening structure of the anti-scatter grid for alignment with respect to the stack structure and the side of the anti-scatter grid facing the converter element, such that the effect of the anti-scatter grid is advantageously not adversely affected by the reflection unit and/or the light-directing unit.

Advantageously, the conditioning of the converter material can be improved. Advantageously, the negative drift characteristics of the converter material and thus the counting rate drift of the evaluation unit can be reduced, as well as unwanted image artifacts being reduced. Advantageously, a stable and permanently good image quality can be achieved during operation.

According to one embodiment of the invention, the light-directing unit comprises a light guide. The light guide can be curved. The light guide can, for example, comprise a fiber optic. Advantageously, an arrangement of the light-directing unit on the anti-scatter grid can be avoided. Advantageously, the light-directing unit can be connected to the possible diffuser in a light-conducting manner. Advantageously, the light path can be curved. Advantageously, a complicated alignment of the reflection unit can be avoided. Advantageously, losses in the quantity of light along the light path can be reduced. Advantageously, the quantity of light can be coupled directly at the light source into the light guide. Advantageously, the possible evaluation unit and the lateral surfaces of the converter element can be protected from unwanted incidence of light.

According to one embodiment of the invention, the light guide partially runs through a recess of a further carrier element. A further carrier element may be formed between the converter element and/or the possible evaluation unit and the carrier element. The further carrier element can be a carrier ceramic and the carrier element can be the so-called module backplane. The light source can be arranged on the module backplane. Advantageously, the distance of the light source from the heat-sensitive converter element can be increased. Advantageously, a larger heat sink can be connected to the carrier element in a thermally conductive manner. The light path and/or the light-guiding element, particularly the light guide, can be guided through a recess in the further carrier element. A thermal connection of the light source can be formed via a thermal through-connection in the carrier element to a heat sink and/or a metallic contact, for example a holding device of the X-ray detector. Advantageously, the heat of the light source can be dissipated with greater ease.

According to one embodiment of the invention, the carrier element comprises a thermal through-connection. The thermal through-connection can essentially be formed parallel to the stacking direction in the carrier element. The thermal through-connection can have a thermally conductive connection to the light source. Advantageously, the thermal conductivity of the carrier element can be improved. The carrier element can be advantageously connected in a thermally optimized manner via thermally conductive adhesive to a holding device of the X-ray detector or a heat sink and/or heat accumulator/conductor. Advantageously, cooling via cooling air can be optimized. The thermal conductivity of the carrier element can be advantageously improved via the thermal through-connection, for example by a factor of up to 100 when the light source is arranged on a ceramic material in relation to a light source arranged on FR-4 without thermal through-connection.

According to one embodiment of the invention, the carrier element comprises an electrically insulating carrier material, a composite material or a ceramic material. The ceramic material can preferably be HTCC or LTCC. The ceramic material can have a coefficient of heat transfer from 3 to 20 W/m*K. The composite material can be FR-4. The composite material can have a coefficient of heat transfer of approx. 0.3 W/m*K. Advantageously, the cooling of the light source can be optimized.

According to one embodiment of the invention, the light-directing unit is arranged on a surface of an anti-scatter grid facing the converter element. The light guide can be arranged along the surface and/or side of the anti-scatter grid facing the converter element. The reflection unit can be arranged on a surface and/or side of the anti-scatter grid facing the converter element. Advantageously, the anti-scatter grid can be used to align the light path.

According to one embodiment of the invention, the stack arrangement also has an evaluation unit between the converter element and the carrier element. The electric pulses can be evaluated directly in the evaluation unit. Advantageously, the data streams can be combined close to the converter element.

According to one embodiment of the invention, the evaluation unit or the light guide comprises a light screen which is opaque for the quantity of light. The evaluation unit can have an opaque light screen, for example a coating, on the lateral surfaces parallel to the stacking direction. The light guide can have an opaque light screen, for example a coating which is opaque for the wavelength of the light source. Advantageously, the light-sensitive evaluation unit can be protected from the incidence of light. Advantageously, influencing of the evaluation unit by the light path and/or the light source can be reduced and/or avoided.

According to one embodiment of the invention, the light source emits infrared, visible or ultraviolet light. The light source can be designed as an LED. The light source can preferably emit infrared light. The wavelength of the light source can be adjustable. The quantity of light and/or light output of the light source can be adjustable. Advantageously, the conditioning of the converter material can be optimized.

At least one embodiment of the invention further relates to a medical device having an X-ray detector according to the invention. The advantages of the X-ray detector according to at least one embodiment of the invention can be transferred to the medical device. Advantageously, image artifacts can be reduced.

According to at least one embodiment of the invention, the medical device is a computed tomography system. Advantageously, the cooling and/or heat dissipation from the light source can be designed in a space-efficient manner such that necessary space inside the rotor for cooling the light source can be minimized.

Figure 1:
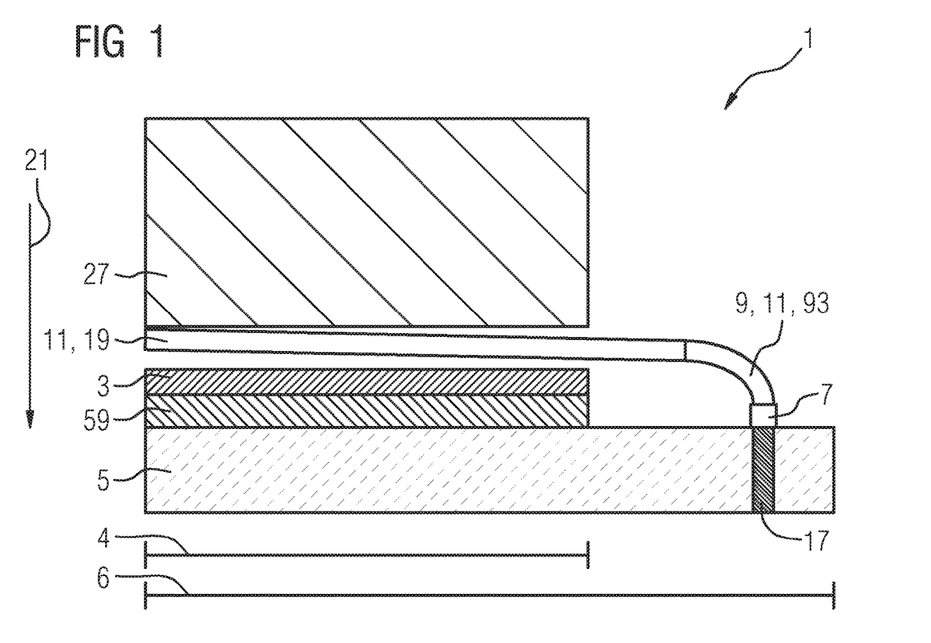
FIG. 1 A diagrammatic view of an X-ray detector according to an embodiment of the invention in a first embodiment.

FIG. 1 shows an example embodiment of the X-ray detector 1 according to the invention in a first embodiment. The X-ray detector 1 has a converter element 3 and a carrier element 5 in a stack arrangement. A light source 7 is arranged on the carrier element 5. A light-directing unit 9, 93 is formed outside a projection of the planar extension of the converter element 3 in the stacking direction 21. The light-directing unit 9, 93 is arranged such that a quantity of light emitted by the light source 7 by way of a light path 11 is incident on the surface of the converter element 3 facing away from the carrier element 5. A planar extension 6 of the carrier element 5 is larger than a planar extension 4 of the converter element 3. The light source 7 is arranged outside the projection of the converter element 3 in the stacking direction 21. The light-directing unit 9, 93 comprises a light guide 93. The carrier element 5 comprises a thermal through-connection 17. The carrier element 5 has an electrically insulating carrier material, a composite material or a ceramic material. The stack arrangement also has an evaluation unit 59 between the converter element 3 and the carrier element 5. The evaluation unit 59 or/and the light guide 9, 93 comprise a light screen which is opaque for the quantity of light. The light source 7 is an LED. The light source 7 emits infrared, visible or ultraviolet light. Preferably, the light source 7 emits infrared light.

The X-ray detector 1 is a directly-converting or counting X-ray detector. The converter element 3 has CdTe or CZT. The X-ray detector 1 has a plurality of pixel elements. The converter element 3 is electrically conductively connected to an evaluation unit 59 via solder joints. The evaluation unit 59 comprises the evaluation electronics. The evaluation unit 59 is electrically conductively connected to the carrier element 5.

The carrier element 5 is a carrier ceramic. The evaluation unit 59 is in particular directly connected to the carrier element 5 and/or the carrier ceramic in an electrically conductively manner. The stack arrangement has the following elements in the following sequence: an anti-scatter grid 27, a light diffuser 19, a converter element 3, an evaluation unit 59 and a carrier element 5.

The converter element 3 has a planar extension 4 perpendicular to the operational direction of radiation incidence of the X-ray radiation and/or stacking direction 21. The planar extension 4 is essentially formed in the stack plane. The surface formed by the planar extension 4 is referred to as the radiation incidence surface. The converter element 3 has a surface normal which is aligned perpendicular to the planar extension 4. The stacking direction 21 runs essentially parallel to the surface normal. The projection of the planar extension 4 of the converter element 3 runs in the stacking direction 21 such that the planar extension 4 of the converter element 3 is projected in a viewing direction along the stacking direction 21 into another plane, in particular another stack plane.

The light source 7 emits a quantity of light which is in particular predetermined and adjustable. The light source 7 is connected to a light-directing unit 9, 93 such that the quantity of light can essentially be completely coupled into the light-directing unit 9, 93 and/or the quantity of light can essentially be completely incident on the converter element 3. The quantity of light is guided along a light path 11 to the converter element 3 via a light-directing unit 9, 93. The light path 11 is curved or kinked or non-linear. The quantity of light is incident on a surface of the converter element 3 facing away from the carrier element 5. The surface of the converter element 3 facing away from the carrier element 5 can in particular face away from the light source 7. The quantity of light cannot and/or in particular cannot completely be incident on the converter element 3 without the light-directing unit 9, 93. The carrier element 5 has HTCC and/or LTCC ceramics. The light source 7 is arranged on the carrier element 5, for example, via a solder joint.

The planar converter element 3 is arranged in relation to the carrier element 5 such that the light source 7 is arranged outside the projection of the planar extension 4 of the converter element 3 in the stacking direction 21 and on the carrier element 5. The light source 7 is arranged laterally next to the evaluation unit 59 on the carrier element 5. The direction angle of the light-directing unit 9, 93 can, for example, be approximately 90 degrees.

The quantity of light can be guided along the light path 11 from the plane of the carrier element 5 at least to the plane of the converter element 3 essentially along the stacking direction 21. The light path 11 partially runs essentially perpendicular to the stacking direction 21, for example as far as the lateral edge of the surface of the converter element 3 or inside a light diffuser 19 essentially parallel to the planar extension 4 of the converter element 3. The light diffuser 19 can be designed such that the quantity of light can be uniformly decoupled from the light diffuser 19 along the planar extension 4 of the converter element 3 such that a homogenous illumination of the converter element 3 can be achieved. The light diffuser 19 can partially comprise the light path 11. The light guide 9, 93 is curved. The light guide 9, 93 comprises, for example, a fiber optic.

The thermal through-connection 17 is designed to be parallel to the stacking direction 21 in the carrier element 5. The thermal through-connection 17 has a thermally conductive connection to the light source 7. The carrier element 5 can be connected in a thermally optimized manner via thermally conductive adhesive to a holding device of the X-ray detector 1 or a heat sink and/or heat accumulator/conductor. The thermal conductivity of the carrier element 5 is improved by the thermal through-connection 17, for example by a factor of up to 100 when the light source 7 is arranged on a ceramic material in relation to a light source arranged on FR-4 without thermal through-connection 17. The ceramic material is preferably HTCC or LTCC. The ceramic material has a coefficient of heat transfer from 3 to 20 W/m*K.

The evaluation unit 59 can have an opaque light screen, for example a coating, on the lateral surfaces parallel to the stacking direction 21. The light guide 9, 93 can have an opaque light screen, for example a coating. The wavelength of the light source can be adjustable. The quantity of light and/or light output of the light source 7 can be adjustable.

Figure 2:
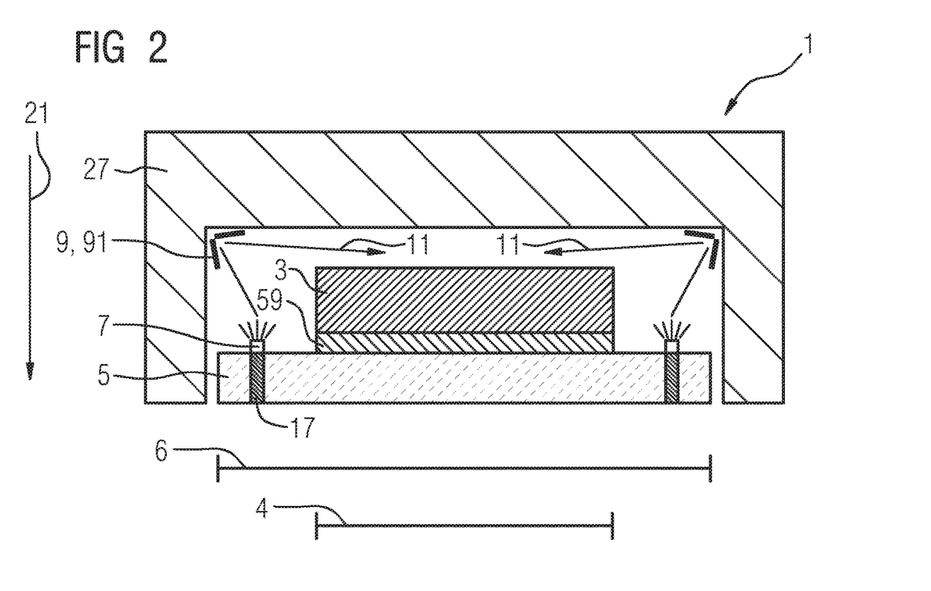
FIG. 2 A diagrammatic view of an X-ray detector according to an embodiment of the invention in a second embodiment.

FIG. 2 shows an example embodiment of the X-ray detector 1 according to the invention in a second embodiment. The light-directing unit 9 comprises a reflection unit 91. The light-directing unit 9, 91 is arranged on a surface of an anti-scatter grid 27 facing the converter element 3. The reflection unit 9, 91 is designed as a mirror. The reflection unit 9, 91 has at least one reflective surface. The reflection unit 9, 91 is designed such that the light path 11 runs from the light source 7 to the surface of the converter element 3 facing away from the carrier element 5. The reflection unit 9, 91 is arranged on the anti-scatter grid 27. The reflection unit 9, 91 is arranged on the anti-scatter grid 27 such that the light path 11 runs from the light source 7 to the reflection unit 9, 91 parallel to the stacking direction 21. The reflection unit 9, 91 is designed such that the light path 11 is deflected to the surface of the converter element 3 facing away from the carrier element 5. The reflection unit 9, 91 is arranged between the fastening structure of the anti-scatter grid 27 for alignment with respect to the stack structure and the side of the anti-scatter grid 27 facing the converter element 3. The reflection unit 9, 91 is arranged on a surface and/or side of the anti-scatter grid 27 facing the converter element.

Figure 3:
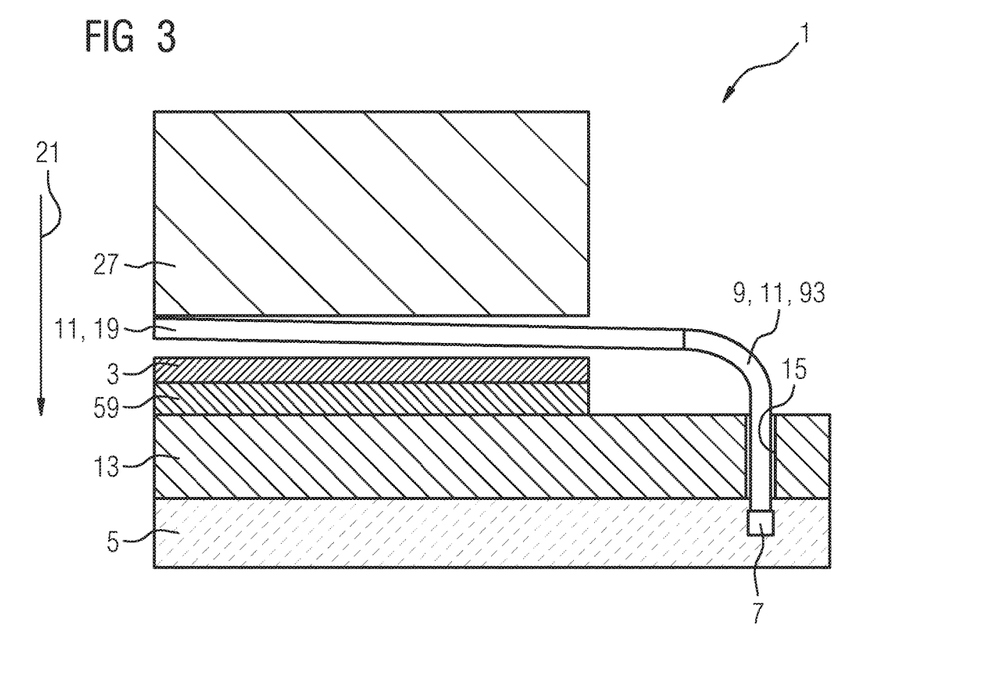
FIG. 3 A diagrammatic view of an X-ray detector according to an embodiment of the invention in a third embodiment.

FIG. 3 shows an example embodiment of the X-ray detector 1 according to the invention in a third embodiment. The light guide 9, 93 partially runs through a recess 15 of a further carrier element 13. The light path 11 partially runs essentially parallel to the stacking direction 21. The stack arrangement has the following elements in the following sequence: an anti-scatter grid 27, a light diffuser 19, a converter element 3, an evaluation unit 59, a further carrier element 13 and a carrier element 5. The carrier element 5 is a so-called module backplane. The evaluation unit 59 is indirectly connected electrically conductively to the carrier element 5 and/or the module backplane by way of a further carrier element 13.

A further carrier element 13 is formed and/or arranged between the converter element 3 and/or the evaluation unit 59 and the carrier element 5. The further carrier element 13 is a carrier ceramic and the carrier element 5 is the so-called module backplane. The light source 7 is arranged on the module backplane. The light path 11 and/or the light-directing unit 9, particularly the light guide 93, is guided through a recess 15 in the further carrier element 13. A thermal connection of the light source 7 can be formed via a thermal through-connection in the carrier element 5 to a heat sink and/or a metallic contact, for example a holding device of the X-ray detector 1 (not shown).

Figure 4:
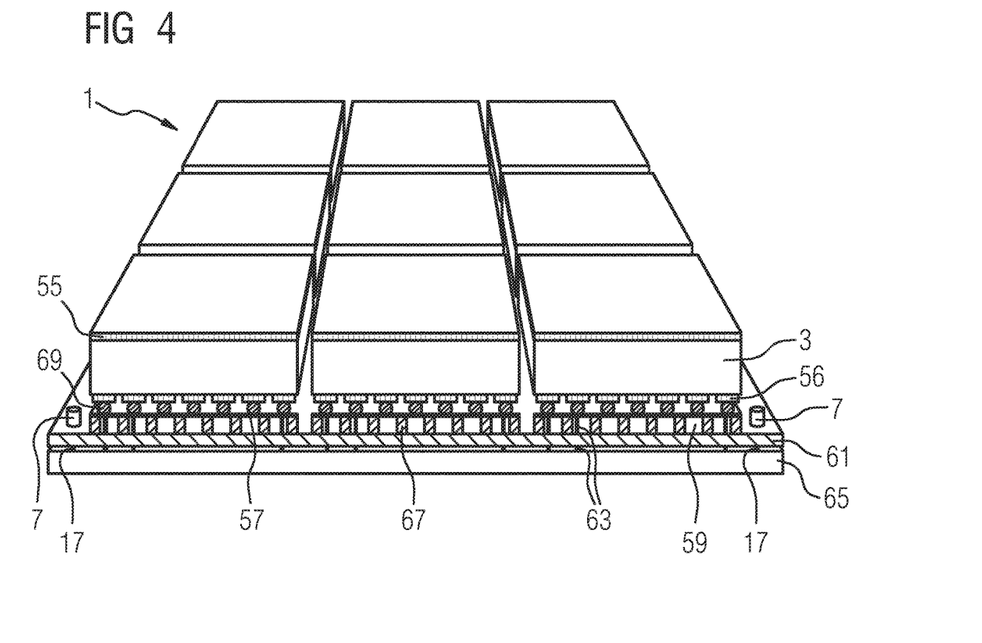
FIG. 4 A diagrammatic view of an X-ray detector according to an embodiment of the invention in a fourth embodiment.

FIG. 4 shows an example embodiment of the X-ray detector 1 according to the invention in a fourth embodiment with an arrangement of a plurality of directly-converting converter elements 3 and evaluation units 59 in stack arrangements. One directly-converting converter element 3 respectively and one evaluation unit 59 respectively are arranged in a stack. In a preferred embodiment, the X-ray detector 1 has a two-dimensional matrix or arrangement of a plurality of detector elements, pixels or subpixels. The number of subpixels may be, for example, in the range of 100 to several thousand. The subpixels can have a plurality of energy channels.

The directly-converting converter element 3 can be designed as a planar direct converter, for example having CdTe, CZT, CdZnTeSe, CdTeSe, CdMnTe, InP, $TlBr_2$, $HgI_2$, GaAs or others as converter material. The first surface of the directly-converting converter element 3 has a top electrode 55. The second surface of the directly-converting converter element 3 has a two-dimensional arrangement of contacts 56 and/or electrodes. The contacts 56 are connected to the pixel electrodes 57 and the pixel electronics 67 in the evaluation unit 59 by way of solder joints 69. The individual pixel electrodes 57 can in particular be separated from one another (not shown). The solder joints 69 can, for example, be designed as solder balls (bump bonds or bump balls) or solder material in conjunction with copper pillars.

The number of contacts 56, the number of solder joints 69, the number of pixel electrodes 57 and the number of pixel electronics 67 in the evaluation unit 59 are equal. The electric field between the top electrode 55 and a contact 56 determines a sensitive detection volume. The entity comprising a detection volume, a contact 56, a solder joint 69, a pixel electrode 57 and pixel electronics 67 connected to the pixel electrode 57 forms a detector element. The evaluation unit 59 is connected to a substrate 61 on the underside. The light source 7 is arranged on the substrate 61. The light source 7 is connected to a thermal through-connection 17 in a thermally conductive manner. The evaluation unit 59 is connected to peripheral electronics 65 by way of TSV connections 63 through the substrate 61. For the purposes of clarity, the anti-scatter grid, the light path and the light-directing unit are not shown in this view.

Figure 5:
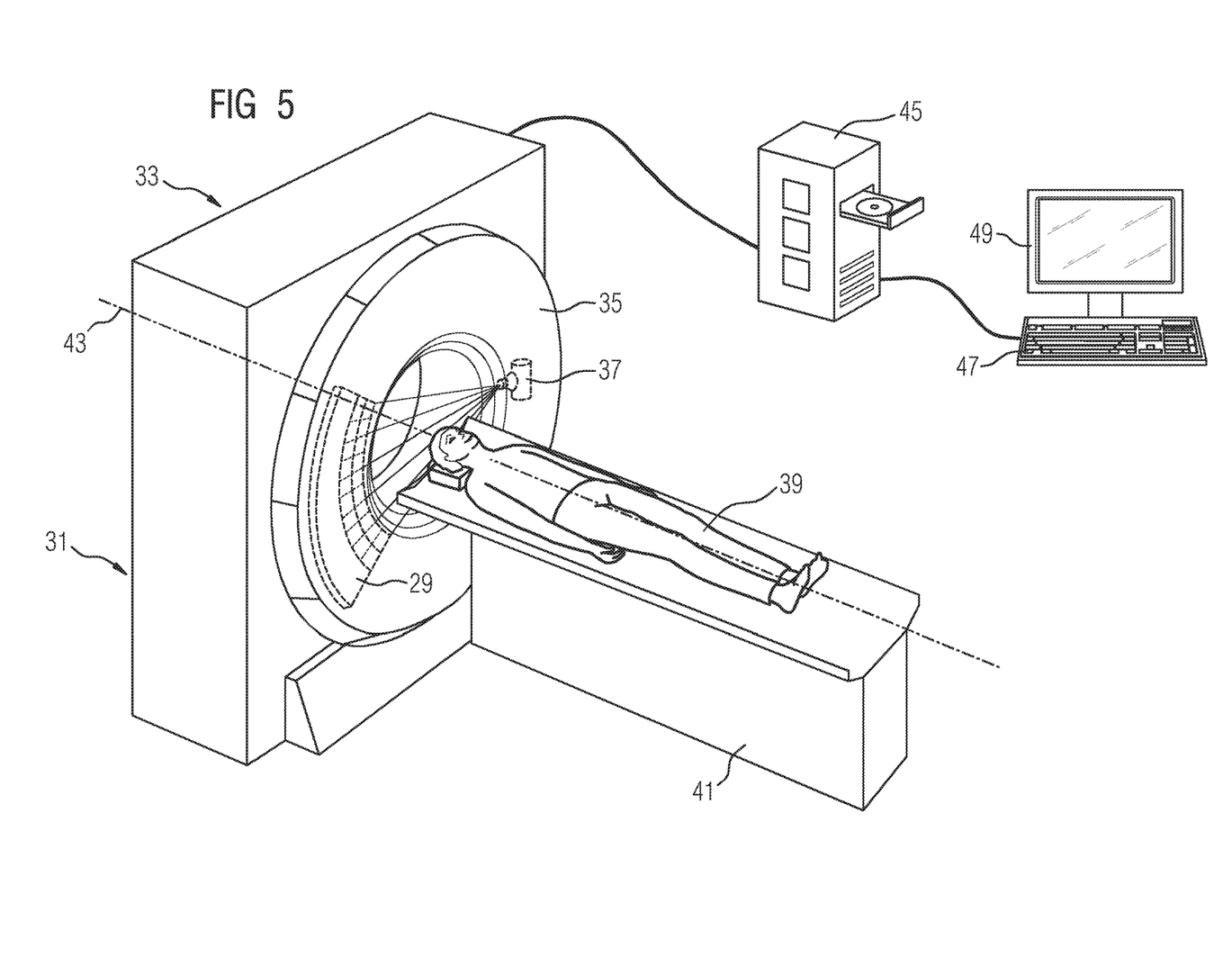
FIG. 5 A diagrammatic view of a computed tomography system according to an embodiment of the invention.

FIG. 5 shows an example embodiment of a computed tomography system 31 according to the invention with an X-ray detector 1 according to the invention. The computed tomography system 31 contains a gantry 33 with a rotor 35. The rotor 35 comprises an X-ray source 37 and a detector device 29 with a plurality of X-ray detectors according to the invention. The patient 39 is supported on the patient couch 41 and can be moved along the rotational axis z 43 through the gantry 33. An arithmetic unit 45 is used to control and calculate the cross-sectional images. An input device 47 and an output device 49 are connected to the arithmetic unit 45.

Although the invention was illustrated in more detail by the preferred example embodiment, the invention is not limited by the disclosed examples and other variations can be derived therefrom by a person skilled in the art without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector, comprising:
   a converter element;
   a carrier element, the converter element and the carrier element being arranged in a stack arrangement;
   a light source, arranged on the carrier element;
   a light-directing unit, formed outside a projection of a planar extension of the converter element in a stacking direction of the stack arrangement, the light-directing unit being arranged such that a quantity of light, when emitted by the light source, is incident on a surface of the converter element, facing away from the carrier element via a light path.

2. The X-ray detector of claim 1, wherein a planar extension of the carrier element is relatively greater than a planar extension of the converter element.

3. The X-ray detector of claim 2, wherein the light source is arranged outside the projection of the converter element in the stacking direction.

4. The X-ray detector of claim 2, wherein the light path partially runs essentially parallel to the stacking direction.

5. The X-ray detector of claim 2, wherein the light-directing unit includes a reflection unit.

6. The X-ray detector of claim 2, wherein the light-directing unit includes a light guide.

7. A medical device comprising the an X-ray detector of claim 2.

8. The medical device of claim 7, wherein the medical device is a computed tomography system.

9. The X-ray detector of claim 1, wherein the light path partially runs essentially parallel to the stacking direction.

10. The X-ray detector of claim 1, wherein the light-directing unit includes a reflection unit.

11. The X-ray detector of claim 1, wherein the light-directing unit includes a light guide.

12. The X-ray detector of claim 11, wherein the light guide partially runs through a recess of a further carrier element.

13. The X-ray detector of claim 11, wherein the light-directing unit is arranged on a surface of an anti-scatter grid facing the converter element.

14. The X-ray detector of claim 11, wherein the stack arrangement also includes an evaluation unit between the converter element and the carrier element.

15. The X-ray detector of claim 14, wherein the evaluation unit or the light guide includes a light screen opaque for the quantity of light.

16. The X-ray detector of claim 1, wherein the carrier element includes a thermal through-connection.

17. The X-ray detector of claim 1, wherein the carrier element includes an electrically insulating carrier material, a composite material or a ceramic material.

18. The X-ray detector of claim 1, wherein the light source is configured to emit infrared, visible or ultraviolet light.

19. A medical device comprising the an X-ray detector of claim 1.

20. The medical device of claim 19, wherein the medical device is a computed tomography system.

21. The X-ray detector of claim 1, wherein the light-directing unit is arranged on a surface of an anti-scatter grid facing the converter element.

22. The X-ray detector of claim 1, wherein the stack arrangement also includes an evaluation unit between the converter element and the carrier element.

* * * * *